(12) United States Patent
Huebner et al.

(10) Patent No.: US 9,750,796 B2
(45) Date of Patent: Sep. 5, 2017

(54) **CELL WALL POLYMERS OF *ENTEROCOCCUS FAECALIS* AND USES THEREOF**

(71) Applicants: UNIVERSITAETSKLINIKUM FREIBURG, Freiburg (DE); FORSCHUNGSZENTRUM BORSTEL, Borstel (DE)

(72) Inventors: Johannes Huebner, Freiburg (DE); Otto Holst, Bad Oldesloe (DE); Christian Theilacker, Freiburg (DE); Karolina Kruszynska, Basel (CH); Stefan Geiss-Liebisch, Freiburg (DE); Agnieszka Beczala, Borstel (DE)

(73) Assignees: UNIVERSITAETSKLINKUM FREIBURG, Freiburg (DE); FORSCHUNGSZENTRUM BORSTEL, Borstel (DE)

( * ) Notice: Subject to any disclaimer, the term of this patent is extended or adjusted under 35 U.S.C. 154(b) by 235 days.

(21) Appl. No.: 14/387,753

(22) PCT Filed: Mar. 4, 2013

(86) PCT No.: PCT/EP2013/054274
§ 371 (c)(1),
(2) Date: Sep. 24, 2014

(87) PCT Pub. No.: WO2013/143806
PCT Pub. Date: Oct. 3, 2013

(65) Prior Publication Data
US 2015/0139998 A1    May 21, 2015

(30) Foreign Application Priority Data
Mar. 30, 2012   (EP) .................................... 12162640

(51) Int. Cl.
| | | |
|---|---|---|
| A61K 31/34 | (2006.01) |
| C07K 14/315 | (2006.01) |
| C07H 15/04 | (2006.01) |
| A61K 39/09 | (2006.01) |
| C07K 16/12 | (2006.01) |
| C08B 37/00 | (2006.01) |
| C12P 19/26 | (2006.01) |
| C12P 19/44 | (2006.01) |
| A61K 39/00 | (2006.01) |

(52) U.S. Cl.
CPC ............. *A61K 39/09* (2013.01); *C07H 15/04* (2013.01); *C07K 16/1228* (2013.01); *C07K 16/1267* (2013.01); *C08B 37/006* (2013.01); *C12P 19/26* (2013.01); *C12P 19/44* (2013.01); *A61K 2039/575* (2013.01); *C07K 2317/30* (2013.01)

(58) Field of Classification Search
None
See application file for complete search history.

(56) References Cited

FOREIGN PATENT DOCUMENTS

WO    WO 2011/088843 A1    7/2011

OTHER PUBLICATIONS

Koch et al. (Vaccine 2004 22: 822-830).*
Amyes SGB (Internatl. J. Antimicrobial Agents 2007 29 (Suppl. 3): s43-s52).*
Gura (Science, 1997, 278:1041-1042).*
Kaiser (Science, 2006, 313: 1370).*
Eduardo Diaz-Rubio (The Oncologist, 2004, 9, 282-294).*
Behr, Thomas et al., "The structure of pneumococcal lipoteichoic acid improved preparation, chemical and mass spectrometric studies," *European Journal of Biochemistry*, 1992, 207(2):1063-1075.
Toivanen, P. et al., "Complement-Fixing Antibodies to Adenovirus in Rabbits and Guinea-Pigs Treated with 6-Mercaptopurine or ε-Aminocaproic Acid," *Acta Pathologica et Microbiologica Scandinavica*, 1965, 63:221-227.

* cited by examiner

*Primary Examiner* — Peter J Reddig
*Assistant Examiner* — Kauser Akhoon
(74) *Attorney, Agent, or Firm* — Saliwanchik, Lloyd & Eisenschenk

(57) ABSTRACT

The present invention relates to enterococcal cell wall polymers and their uses in the prevention and therapy of bacterial infection.

1 Claim, 4 Drawing Sheets

CELL WALL POLYMERS OF ENTEROCOCCUS FAECALIS AND USES THEREOF

CROSS REFERENCE TO RELATED APPLICATIONS

Figure 1:
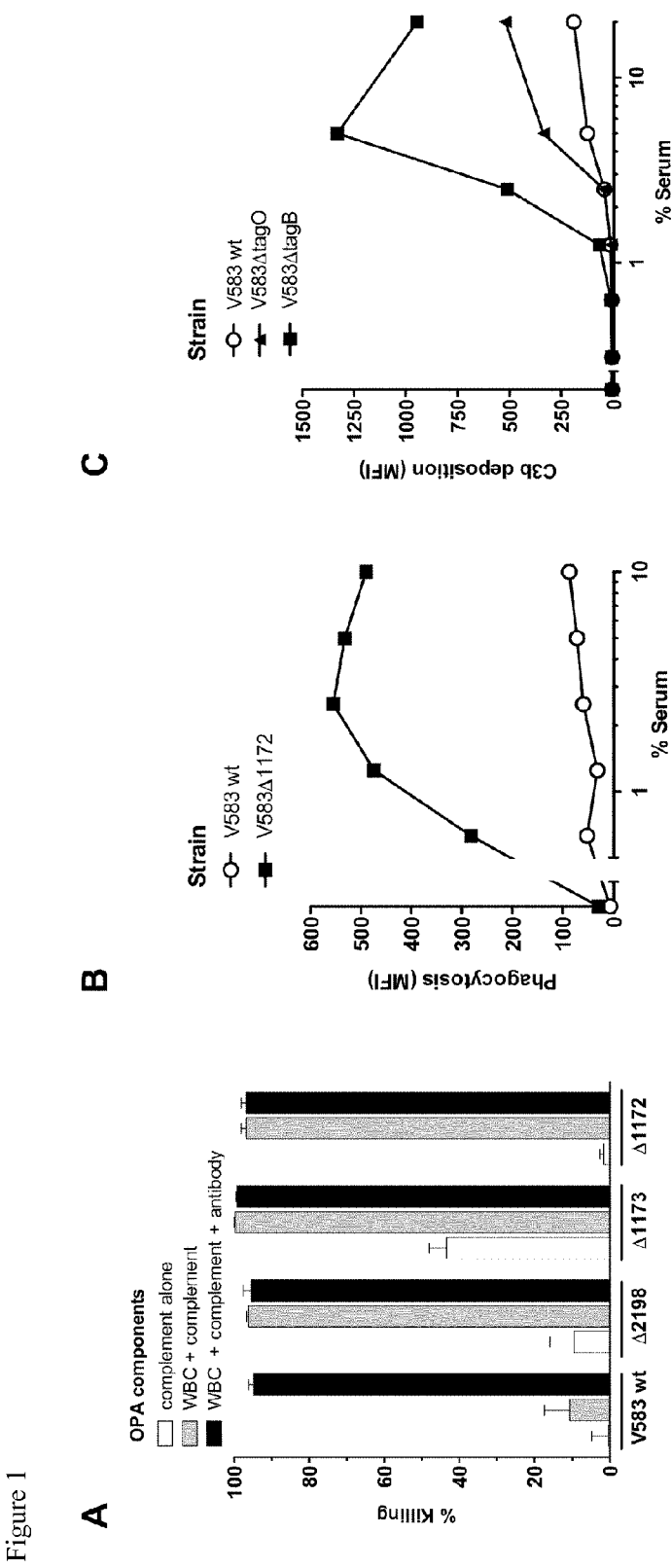

This application is a National Stage Application of International Application Number PCT/EP2013/054274, filed Mar. 4, 2013; which claims priority to European Patent Application No. 12162640.2, filed Mar. 30, 2012; which are incorporated herein by reference in their entirety.

The present invention relates to enterococcal cell wall polymers and their uses in the prevention and therapy of bacterial infection.

BACKGROUND OF THE INVENTION

*Enterococcus faecalis* is an important nosocomial pathogen and a frequent cause of infection in critically ill patients (Vincent J L, et al. International study of the prevalence and outcomes of infection in intensive care units. JAMA. 2009 Dec. 2; 302(21): 2323-9). Underlying malignancy, neutropenia, antineoplastic chemotherapy and immunosuppressive medication are well-characterized risk factors for invasive infections with enterococci (Ghanem G, et al. Outcomes for and risk factors associated with vancomycin-resistant *Enterococcus faecalis* and vancomycin-resistant *Enterococcus faecium* bacteremia in cancer patients. Infect Control Hosp Epidemiol. 2007 September; 28(9): 1054-9; Diaz-Granados C A, Jernigan J A. Impact of vancomycin resistance on mortality among patients with neutropenia and enterococcal bloodstream infection. J Infect Dis. 2005 Feb. 15; 191(4):588-95; Peel T, et al. Differing risk factors for vancomycin-resistant and vancomycin-sensitive enterococcal bacteraemia. Clin Microbiol Infect. 2012 April; 18(4): 388-94. Epub 2011 Aug. 16) and the clinical outcome of invasive enterococcal infections in this patient population is frequently poor (Theilacker C, Jonas D, Huebner J, Bertz H, Kern W. Outcomes of Invasive Infection due to Vancomycin-Resistant *Enterococcus faecium* during a Recent Outbreak. Infection. 2009 December; 37(6):540-3). Risk factors that may contribute to the increased susceptibility of high-risk groups to enterococcal infection include high-density colonization of the gastrointestinal tract (Ubeda C, et al. Vancomycin-resistant *Enterococcus* domination of intestinal microbiota is enabled by antibiotic treatment in mice and precedes bloodstream invasion in humans. J Clin Invest. 2010 Dec. 1; 120(12): 4332-41), damage to the gastrointestinal mucosal barrier, indwelling devices such as central venous catheters, and immune dysregulation (Peel T, et al. Differing risk factors for vancomycin-resistant and vancomycin-sensitive enterococcal bacteraemia. Clin Microbiol Infect. 2012 April; 18(4):388-94. Epub 2011 Aug. 16).

The complement system is an important first line of defense against invasive infections and plays a critical role in the immuno-compromised host with defective adaptive immunity. It comprises more than 30 proteins, which are detectable in human serum, on cell surfaces and in tissue fluids. The classical-, alternative- and lectin pathway all converge in the cleavage of C3 to form C3b, the key effector molecule of the complement system. Complement receptor 3 of neutrophils binds C3b deposited on the bacterial envelope leading to phagocytosis and killing of the ingested bacterium. Studies in C3-depleted mice have demonstrated that C3 is also critical for opsonphagocytosis and clearance of enterococci from infected organs (Leendertse M, et al. The complement system facilitates clearance of *Enterococcus faecium* during murine peritonitis. J Infect Dis. 2010 Feb. 15; 201(4): 544-52). In addition, multiple epidemiologic studies have shown that a deficiency of mannose-binding lectin—the best described factor of the lectin pathway—predisposes to severe infection and bacteremia in neonates, neutropenic patients and patients after allogeneic stem cell or solid organ transplantation (Vekemans M, et al. Low mannose-binding lectin concentration is associated with severe infection in patients with hematological cancer who are undergoing chemotherapy. Clin Infect Dis. 2007 Jun. 15; 44(12): 1593-601; Schlapbach L J, et al. Differential role of the lectin pathway of complement activation in susceptibility to neonatal sepsis. Clin Infect Dis. 2010 Jul. 15; 51(2): 153-62; Worthley D L, et al. Donor mannose-binding lectin deficiency increases the likelihood of clinically significant infection after liver transplantation. Clin Infect Dis. 2009 Feb. 15; 48(4):410-7; Mullighan C G, et al. Mannose-binding lectin status is associated with risk of major infection following myeloablative sibling allogeneic hematopoietic stem cell transplantation. Blood. 2008 Sep. 1; 112(5): 2120-8).

In the course of evolution, Gram-positive bacteria have developed numerous strategies to escape recognition and targeting by the complement system. The flexibility of pathogens to circumvent binding of complement factors is illustrated impressively by *Staphylococcus aureus* (Serruto D, Rappuoli R, Scarselli M, Gros P, van Strijp J A. Molecular mechanisms of complement evasion: learning from staphylococci and meningococci. Nat Rev Microbiol. 2010 June; 8(6): 393-9). In contrast, little is known about the interaction of *E. faecalis* and the complement system.

Toivanen P et al.: "Complement-fixing antibodies to adenovirus in rabbits and guinea-pigs treated with 6-mercaptopurine or epsilon-aminocaproic acid", 1965, Acta Pathologica et Microbiologica Scandinavica 1965, Vol. 63, pages 221-227 and T Behr, et al. "The structure of pneumococcal lipoteichoic acid. Improved preparation, chemical and mass spectrometric studies" FEBS J 207(3):1063-75 (1992) describe compounds which comprise a group consisting of β-D-GalpNac-ribitol structures. However, structures wherein R1 is selected from β-D-Glcp or α-L-Rhap and R2 is selected from β-D-Glcp or H are not disclosed.

WO 2011/088843 describes enterococcal cell wall components and their uses in the prevention and therapy of bacterial infection.

In order to provide more efficient strategies to effectively treat and/or prevent infection in vertebrates caused, at least in part, by enterococci, new antigenic bacterial targets are needed which could be used in new and improved vaccination strategies, as well as in the development and production of respective vaccines.

Glycolipids, teichoic acids (TA) and wall teichoic acids (WTA) could serve as potential targets for new drugs for the treatment of Gram-positive bacterial infection. Although cell wall polysaccharide is a main component of the cell wall of Gram-positive bacteria as well, little is known about any potential antigens derived from this class of components.

As a part of the search for carbohydrate complement resistance factors and the development of alternative treatments such as glycoconjugate vaccines to combat enterococcal infections, the present invention fulfils these need by providing new capsular polysaccharides isolated from the cell wall of enterococci.

Thus, the objects of the present invention in a first aspect thereof are solved by an enterococcal cell wall component selected from the group consisting of β-D-GalpNAc-ribitol structures

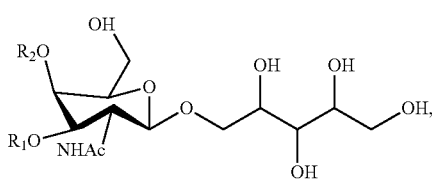

(I)

wherein $R_1$ is selected from β-D-Glcp or α-L-Rhap, and $R_2$ is selected from H or α-D-Glcp,
and derivatives thereof, and pharmaceutically acceptable salts thereof, wherein Rhap is 6-deoxy-mannopyranose (rhamnose); GalpNAc is 2-acetamido-2-deoxy-galactopyranose (N-acetyl-galactosamine); and Glcp is glucopyranose.

Preferably, $R_1$ is selected from β-D-Glcp according to the following formula II

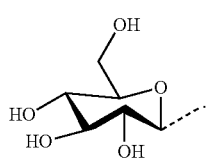

II

Preferably, $R_1$ is selected from α-L-Rhap according to the following formula III

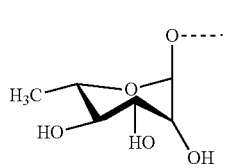

III

Preferably, $R_2$ is selected from α-D-Glcp, according to the following formula IV

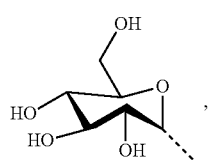

IV wherein the dashed lines in II to IV indicate the connection to the β-D-GalpNAc-ribitol structure as above.

Figure 4:
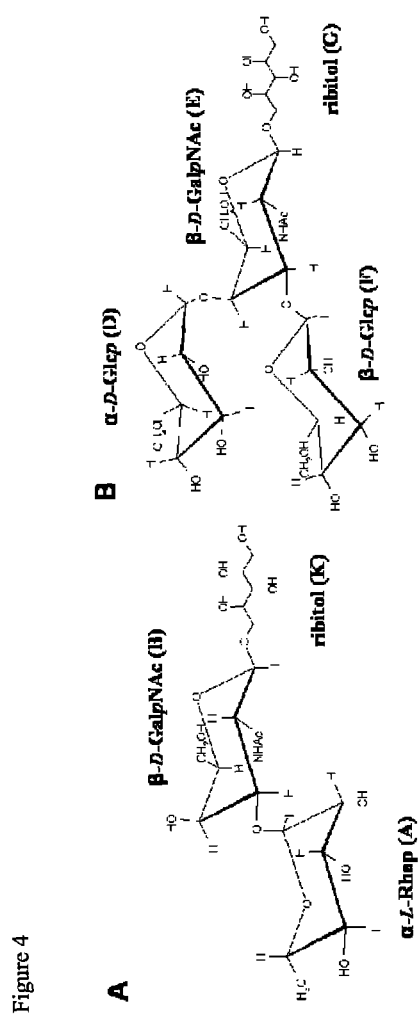

Most preferred are the structures OS I and/or OS II as shown in FIG. 4.

In the context of the present invention, the interaction of carbohydrate cell surface structures of E. faecalis with the human complement system was investigated. Previously, a library of 177 targeted insertion mutants of genes involved in putative surface or stress-response factors was constructed in E. faecalis strain V583, and the mutant library was screened for sensitivity to oponophagocytic killing and three mutants of genes putatively involved WTA biosynthesis were readily killed by complement and neutrophils in the absence of specific Ab (Rigottier-Gois L, et al. Large-Scale Screening of a Targeted Enterococcus faecalis Mutant Library Identifies Envelope Fitness Factors. PLoS ONE. 2011 Dec. 15; 6(12): e29023). In contrast, wild type E. faecalis is resistant to killing by complement and neutrophils alone. The present invention is based on the mechanism of increased susceptibility to complement-mediated opsonphagocytosis and the characterization of structural differences of wild type and mutant cell wall accessory carbohydrate polymers.

Three insertional mutants of the wall teichoic acid (WTA) synthesis genes tagA, tagB and tagO in E. faecalis strain V583 were identified which exhibited an increased susceptibility to complement-mediated opsonophagocytosis by neutrophils. Further studies revealed a role of L-ficolin/mannose-binding lectin-associated serine protease (MASP) complexes in $Ca^{2+}$-dependent, Ab-independent opsonophagocytosis of E. faecalis V583Δ1172. To understand the mechanism of lectin pathway activation by E. faecalis V583Δ1172, the inventors structurally characterized cell wall fragments of E. faecalis wild type and V583Δ1172 obtained by enzymatic digestion of peptidoglycan. Cell wall fragments of V583Δ1172 lacked the two oligosaccharides according to the present invention with the structure α-L-Rhap-(1→3)-β-D-GalpNAc-(1→1)-ribitol and α-D-Glcp-(1→4)-[β-D-Glcp-(1→3)-]β-D-GalpNAc-(1→1)-ribitol suggesting the absence of WTA in the mutant.

Thus, the enterococcal cell wall component (in the following also designated as "enterococcal antigen") provides a new antigenic target for the development of more efficient strategies to effectively treat and/or prevent infection in vertebrates caused, at least in part, by enterococci, allow for improved vaccination strategies, and allow the development and production of respective vaccines, such as glycoconjugate vaccines.

According to the present invention, the term a "modified derivative" or "modified derivatives" shall include chemically or enzymatically modified enterococcal antigens according to the formula I as above, wherein said modified derivative maintains its function as an enterococcal antigenic determinant and/or to the same, or substantially the same, extent as the enterococcal antigen according to formula I. Preferably, said modified derivative exhibits a quantitatively increased immunological reaction, compared to a non-modified enterococcal antigen. Such increase of the immunological reaction can be detected with immunological assays known in the art.

Examples for modified derivatives are preferably compounds of formula I that are modified to include a linker group in order to be coupled or conjugated to other chemical entities. These linker groups are known in the state of the art, and usually are immunologically inactive, i.e. do not substantially interfere with the immunological properties of the enterococcal antigen. Other modifications include the addition of chemical moieties of the enterococcal antigen in order to carry a detectable label, such as chelating groups or enzymatic groups. Furthermore, peptide (e.g. His) or other "labels" or "tags" can be added in order to be able to purify and/or use the enterococcal antigen in diagnostic assays.

Finally, the enterococcal antigen can include chemical modifications, for example at the rings of the sugar components of the enterococcal antigen, wherein the antigen can be modified to replace an existing side group with either H, an unsubstituted, monosubstituted or polysubstituted $C_1$-$C_{18}$- alkyl, wherein said alkyl can be straight, branched or cyclic, alkenyl, an unsubstituted, monosubstituted or polysubstituted aryl or heteroaryl residue, an unsubstituted, monosubstituted or polysubstituted benzene group, an acyl group, such as formyl, acetyl, trichloroacetyl, fumaryl, maleyl, succinyl, benzoyl, or a branched or heteroatom or aryl substituted acyl group, an alkoxy substituent, such as —OMe, —OEt, —OnPr, -iPr, —OnBu, —OiBu, —OsecBu, —OtBu, whose alkyl group can be branched, straight or cyclic, an alkyl group bound via a sulphur atom such as —SMe, —SEt, or a sulfonyl group, such as —SO$_3$H, —SO$_2$Me, —SO$_2$CF$_3$, —SO$_2$C$_6$H$_4$CH$_3$ or SO$_2$C$_6$H$_4$CH$_2$Br, or a nitrogen substituent, such as NH$_2$, NHR, —NRR' (with R, R'=alkyl, alkenyl or aryl as above), NC or —NO$_2$, or fluoro, chloro, bromo, iodine, —CN or a heterosubstituent. As mentioned above, these derivatives are preferably included in order to improve the solubility of the antigen, increase the immunological effect of said antigen (preferably quantitatively), and/or to allow the compound to be coupled to other moieties, e.g. in order to be coupled to a surface (such as a well or chip), and/or to be used in diagnostic assays.

Another aspect of the invention relates to a method for producing the enterococcal cell wall component according to the present invention, wherein said method comprises isolating said enterococcal cell wall component from a bacterial fraction, or comprising synthesizing said antigen, at least in part, through chemical synthesis. Isolation can include purifying said cell wall component from bacterial fractions to be substantially free of other bacterial components, but can also include the isolation as part of certain bacterial fractions, such as cell wall fractions including other parts of the cellular wall, as described herein.

Another aspect of the invention relates to an antibody, preferably a monoclonal antibody or antigenic fragment thereof, that specifically recognizes an enterococcal antigen according to the present invention. The term "antibody" shall include both monoclonal or polyclonal antibodies, recombinant antibodies or fragments thereof, such as Fab and the like, as well as human or humanized antibodies.

Another aspect of the invention then relates to a method for producing the antibody according to the present invention, comprising immunizing a mammal, preferably a rabbit, with an enterococcal cell wall component according to the present invention, or a with the pharmaceutical composition according to the present invention, and preferably the vaccine according to the present invention. Respective methods are known to the person of skill, and are disclosed in the state of the art.

Yet another aspect of the present invention then relates to a method for producing the antibody according to the present invention, comprising generating hybridoma cells producing said antibody as a monoclonal antibody, or comprising a recombinant production of said antibody in a host cell. Respective methods are known to the person of skill, and are disclosed in the state of the art Still another important aspect of the present invention then relates to a strain of *E. faecalis* wherein insertional mutants in at least one of the WTA synthesis genes tagA, tagB and tagO are present, such as, for example, strain *E. faecalis* V583Δ1172. This strain can be used in assays and screening tests according to the present invention, e.g. for specific and/or effective antibodies as described herein, or for the screening and identification of specific compounds (such as small molecules) able to inhibit production of above-mentioned antigen.

Still another important aspect of the present invention then relates to the use of the enterococcal antigen according to the present invention as an antigen in the production of antibodies that are specific for said antigen.

Another aspect of the invention then relates to a pharmaceutical composition, comprising at least one enterococcal antigen according to the present invention and/or at least one antibody according to the present invention, together with a pharmaceutically acceptable carrier and/or excipient.

Particularly preferred is a pharmaceutical composition according to the present invention, wherein said composition comprises a cell wall component according to formula I, namely a respective cell wall polysaccharide.

Further preferred is a pharmaceutical composition according to the present invention, wherein said composition is formulated as a vaccine, in particular against infections caused by enterococci, in particular antibiotic-resistant enterococci, such as VRE strains, preferably of *E. faecalis*. Most preferred is a pharmaceutical composition according to the present invention, wherein said cell wall component according to formula I is present in a glycoconjugate vaccine.

The cell wall polysaccharide according to the present invention (either present as the antigen alone or in an extract or bacterium as described herein) is preferably used for an enterococci-vaccine, either for active or passive immunization.

Thus, according to the invention, there is provided a pharmaceutical composition, and in particular a vaccine, for the prevention of enterococcal infections in a vertebrate, said pharmaceutical composition comprising at least one new enterococcal antigen according to the present invention, optionally together with a pharmaceutically acceptable carrier, adjuvants and/or diluent.

Typically, the vaccine can comprise live or dead intact cells of at least one enterococcal strain, preferably of *E. faecalis*, comprising the enterococcal antigen of the invention. More typically, the vaccine comprises cell lysate from at least one of said enterococcal strains as comprising the enterococcal antigen or antigens. Even more typically, the vaccine comprises a crude enterococcal antigen mixture or purified enterococcal antigen or enterococcal antigens from at least one of said enterococcal strains, preferably *E. faecalis*. Still more typically, the vaccine comprises a fraction of the cell wall and associated proteins as enterococcal antigen of at least one of said enterococcal strains. The vaccine may also be comprised of a combination of one of the components. Most preferred is a glycoconjugate vaccine comprising an enterococcal antigen according to the present invention. Another aspect relates to a pharmaceutical composition or vaccine, wherein the enterococcal antigen as included has been produced, at least in part, through chemical synthesis. The methods for purifying the selected bacterial fractions containing enterococcal antigens are known to the person of skill, and are further described herein.

Typically, the vertebrate is a monogastric, herbivore or ruminant animal or human subject. Even more typically, the vertebrate is selected from the group consisting of human, non-human primate, murine, bovine, ovine, equine, porcine, caprine, leporine, avian, feline and canine. More typically, the vertebrate is selected from the group consisting of human, ovine, camelids, porcine, bovine, equine or canine.

The pharmaceutical composition can be formulated for administration via intramuscular, subcutaneous, topical or other parenteral route. In general, the microorganisms of the present invention are commensal in nature. Thus, oral administration is generally not an effective route of vaccination, and as a consequence, administration via an intramuscular, subcutaneous topical or other parenteral route is preferred. The vaccine may also include cytokines, such as: G-CSF, GM-CSF, interleukins or tumor necrosis factor alpha, used singly or in combination.

The pharmaceutical composition may also include an adjuvant. More typically, the adjuvant is selected from the group consisting of Freund's complete/incomplete adjuvant, montenide macrol adjuvant, phosphate buffered saline and mannan oil emulsions, saponins (QuiLA) dextran (dextran sulphate, DEAE-Dextran), aluminum compounds (Imject Alum), N-acetylglucosamiyl-N-acetylmuramyl-L-alanyl-D-isoglutamine (Gerbu adjuvant). More typically, the adjuvant is selected from the group as described in the Vaccine 1995, vol 13, p 1203; 1993 vol 11 p 293; and 1992 vol 10 p 427, the disclosures of which are incorporated herein by reference.

Yet another important aspect of the present invention then relates to an enterococcal cell wall component (enterococcal antigen) according to the present invention, the antibody according to the present invention, or the pharmaceutical composition according to the present invention for use in the treatment of diseases, such as bacterial infections, in particular enterococcal infection, such as nosocomial bacteremia infection, endocarditis, urinary tract infections, surgical wound infections, and foreign body infections.

Yet another important aspect of the present invention then relates to the use of the enterococcal cell wall component according to the present invention, the antibody according to the present invention, or the pharmaceutical composition according to the present invention (i.e. the enterococcal antigens) for the treatment against bacterial infections or for the preparation of a medicament against bacterial infections, in particular enterococcal infection, such as nosocomial bacteraemia infection, endocarditis, urinary tract infections, surgical wound infections, and foreign body infections, in particular caused by antibiotic-resistant gram-positive cocci, such as enterococci, VRE strains, or such as *E. faecalis*.

According to yet another preferred embodiment of the invention, there is provided a method for inducing an immune response against at least one enterococcal strain comprising the enterococcal antigen of the present invention in a vertebrate, said method comprising administering to said vertebrate an immunologically effective amount of the vaccine in accordance with the invention, or a pharmaceutical composition in accordance with the invention.

According to yet another preferred embodiment of the invention, there is provided a method for treating or preventing a bacterial infection in a vertebrate, comprising administering to said vertebrate a therapeutically effective amount of the enterococcal cell wall component according the present invention, the antibody according to the present invention, or the pharmaceutical composition according to the present invention.

Preferred is a method according to the present invention, wherein said bacterial infection is an enterococcal infection, such as nosocomial bacteraemia, endocarditis, a urinary tract infection, surgical wound infection, and foreign body infection, and is particular caused by antibiotic resistant enterococci, such as a VRE strain, and in particular *E. faecalis*.

To examine the role of WTA in the resistance to complement-mediated opsonophagocytosis, the inventors searched for *E. faecalis* genes with similarity to genes involved in the biosynthesis of WTA in *Bacillus subtilis* and *Staphylococcus aureus* using BLAST analysis. Compared to *B. subtilis*, the *E. faecalis* V583 chromosome carries only one teichoic acid glycerol (tag) operon, comprising TagB (EF_1172) and TagA (EF_1173). These two genes are followed by a gene of unknown function (EF_1174) and TagD (63% identity 80% similarity with TarA in *B. subtilis* W23, a glycerol-3-phosphate cytidylyltransferase; EF_1175). The most obvious homologue of the enzyme which catalyzes the first step of WTA biosynthesis, TagO, in V583 is protein EF_2198 (41% identity, 65% similarity with TagO in *S. aureus* COL). Previous work, however, has linked this gene also to the epa locus, which is the gene cluster involved in the biosynthesis of the enterococcal cell-wall polysaccharide, also called enterococcal polysaccharide antigen. Interestingly, a disruption mutant of EF_2198 in *E. faecalis* OG1RF still expressed the cell wall polysaccharide as assessed by agarose gel electrophoresis and reactivity to specific Abs (Teng F, Singh K V, Bourgogne A, Zeng J, Murray B E. Further characterization of the epa gene cluster and Epa polysaccharides of *Enterococcus faecalis*. Infect Immun. 2009 September; 77(9):3759-67).

In the opsonophagocytic assay, the inventors compared the killing of wild type bacteria and insertional mutants in tagO (EF_2198), tagA (EF_1173) and tagB (EF_1172) in the presence of complement and neutrophils alone or together with Abs specific to enterococcal cell surface antigens. In contrast to the wild type, all three mutants in WTA biosynthesis genes were highly susceptible to serum opsonophagocytic killing depleted of specific Ab. The higher killing strongly correlated with increased phagocytosis by neutrophils and a higher density of C3d bound to the bacterial surface of the mutant strain. Additional experiments excluded that the classical and alternative pathway were involved in the increased deposition of C3b on *E. faecalis* V583Δ1172 and provided evidence that complement deposition was due to activation of the lectin pathway.

In order to identify carbohydrate structures that may serve as ligands for the lectin pathway in *E. faecalis* V583Δ1172, the inventors investigated the structural differences in accessory cell wall polymers between mutant and wild type strain. After enzymatic cleavage of peptidoglycan, the inventors identified a PAS-positive band on SDS-PAGE analysis which has previously been identified as the enterococcal cell wall polysaccharide (Theilacker C, et al. Serodiversity of Opsonic Antibodies against *Enterococcus faecalis* glycans of the Cell Wall Revisited. PLoS ONE. 2011; 6(3):e17839).

In the deletion strain *E. faecalis* V583Δ1172, the characteristic band of the cell wall polysaccharide displayed a much slower migration pattern. In addition, the polysaccharide had lost its ability to bind to the cationic dye Stains All and also did not bind to Q-Sepharose, suggesting a loss of anionic charge. Using size-exclusion and anion-exchange chromatography, the inventors obtained purified cell wall fragments from the wild type *E. faecalis* V583 and the *E. faecalis* V583Δ1172 mutant. Material from the *E. faecalis* V583Δ1172 mutant contained less GalNAc, ribitol and phosphate, indicating a loss of WTA from the cell envelope of the mutant (Weidenmaier C, McLoughlin R M, Lee J C. The zwitterionic cell wall teichoic acid of *Staphylococcus aureus* provokes skin abscesses in mice by a novel CD4+ T-cell-dependent mechanism. PLoS ONE. 2010; 5(10): e13227; Neuhaus F C, Baddiley J. A continuum of anionic charge: structures and functions of D-alanyl-teichoic acids in gram-positive bacteria. Microbiol Mol Biol Rev. 2003 December; 67(4):686-723; Swoboda J G, Campbell J, Meredith T C, Walker S. Wall teichoic acid function, biosynthesis, and inhibition. Chembiochem. 2010 Jan. 4; 11(1):35-45).

A definitive elucidation of the structure of the purified native accessory cell wall polysaccharide by NMR spectroscopy was not possible because of the complex and heterogeneous nature of this carbohydrate in both strains. The inventors therefore depolymerized the cell wall fragments by dephosphorylation with HF. After fractionation by gel chromatography, the inventors obtained three distinct pools. The high molecular mass pool contained Rha, Glc, GlcN, and GalN, indicative of the enterococcal cell wall polysaccharide. Methylation analysis suggested a poly-Rha chain with terminal Glc and hexosamine residues. The medium-sized pool contained Rha, Glc, GlcN, GalN, and peptidoglycan fragments, as indicated by the presence of muramic acid and the amino acids Ala, Glu and Lys in a molar ratio of ~4:1:1, consistent with the composition of *E. faecalis* peptidoglycan (Bouhss A, Josseaume N, Severin A, Tabei K, Hugonnet J E, Shlaes D, et al. Synthesis of the L-alanyl-L-alanine cross-bridge of *Enterococcus faecalis* peptidoglycan. J Biol Chem. 2002 Nov. 29; 277(48):45935-41).

Hence, the oligosaccharide likely represented the linkage unit of the cell wall polysaccharide to peptidoglycan. The small molecular mass pool consisted of GalN, ribitol, Glc, and Rha in a molar ratio of ~3:2:1:1. After further purification steps, two oligosaccharides were detected which were amendable to NMR spectroscopy. The structural analysis revealed two ribitol-containing teichoic acid fragments, namely α-L-Rhap-(1→3)-β-D-GalpNAc-(1→1)-ribitol and α-D-Glcp-(1→4)-[β-D-Glcp-(1→3)-]β-D-GalpNAc-(1→1)-ribitol.

Of note, unsuccessful cleavage of a peptidoglycan bridge linking the streptococcal group B carbohydrate and capsular polysaccharide by mutanolysin has been described previously (Deng L, Kasper D L, Krick T P, Wessels M R. Characterization of the linkage between the type III capsular polysaccharide and the bacterial cell wall of group B *Streptococcus*. J Biol Chem. 2000 Mar. 17; 275(11):7497-504).

In summary, the inventors observed two major differences in the cell wall fragments of *E. faecalis* V583Δ1172 compared to the wild type: a) a higher Rha-content of the putative cell-wall polysaccharide and b) the loss of ribitol-containing teichoic acid in the mutant.

Studies in Gram-positive pathogens have described complement interaction with a variety of bacterial carbohydrate antigens including capsular polysaccharide (Aoyagi Y, Adderson E E, Rubens C E, Bohnsack J F, Min J G, Matsushita M, et al. L-Ficolin/mannose-binding lectin-associated serine protease complexes bind to group B streptococci primarily through N-acetylneuraminic acid of capsular polysaccharide and activate the complement pathway. Infect Immun. 2008 January; 76(1):179-88; Krarup A, Sorensen U B, Matsushita M, Jensenius J C, Thiel S. Effect of capsulation of opportunistic pathogenic bacteria on binding of the pattern recognition molecules mannan-binding lectin, L-ficolin, and H-ficolin. Infect Immun. 2005 February; 73(2):1052-60), peptidoglycan (Nadesalingam J, Dodds A W, Reid K B, Palaniyar N. Mannose-binding lectin recognizes peptidoglycan via the N-acetyl glucosamine moiety, and inhibits ligand-induced proinflammatory effect and promotes chemokine production by macrophages. J Immunol. 2005 Aug. 1; 175(3):1785-94), LTA (Lynch N J, et al. L-ficolin specifically binds to lipoteichoic acid, a cell wall constituent of Gram-positive bacteria, and activates the lectin pathway of complement. J Immunol. 2004 Jan. 15; 172(2):1198-202) and WTA (Park K H, et al. Human serum mannose-binding lectin senses wall teichoic acid Glycopolymer of *Staphylococcus aureus*, which is restricted in infancy. J Biol Chem. 2010 Aug. 27; 285(35):27167-75).

The profound alterations in accessory cell wall polymers result in an increased susceptibility to complement deposition by the lectin pathway and in increased opsonophagocytic killing of mutant bacteria. The results thus highlight the importance of the structure of accessory cell wall polymers in immune evasion from the complement system.

The present invention will now be further described in the following preferred non-limiting examples with reference to the accompanying figures. For the purposes of the present invention, all references as cited herein are incorporated in their entireties.

FIG. 1 shows opsonophagocytosis and complement deposition of *E. faecalis* mutants in WTA biosynthesis. A: Opsonophagocytic killing of *E. faecalis* V583 and WTA biosynthesis mutants in the presence of 1.7% absorbed baby rabbit complement alone, complement in combination with human white blood cells (WBC), or complement, WBC and specific rabbit Ab. Percentage of killing was determined as a relative to colony-forming units from control tubes containing bacteria and WBCs. B: Phagocytosis of FITC-labeled, formalin killed bacteria after 15 min of incubation with human serum. C: C3b deposition on enterococcal bacterial cells measured by FACS after incubation with human serum.

Figure 2:
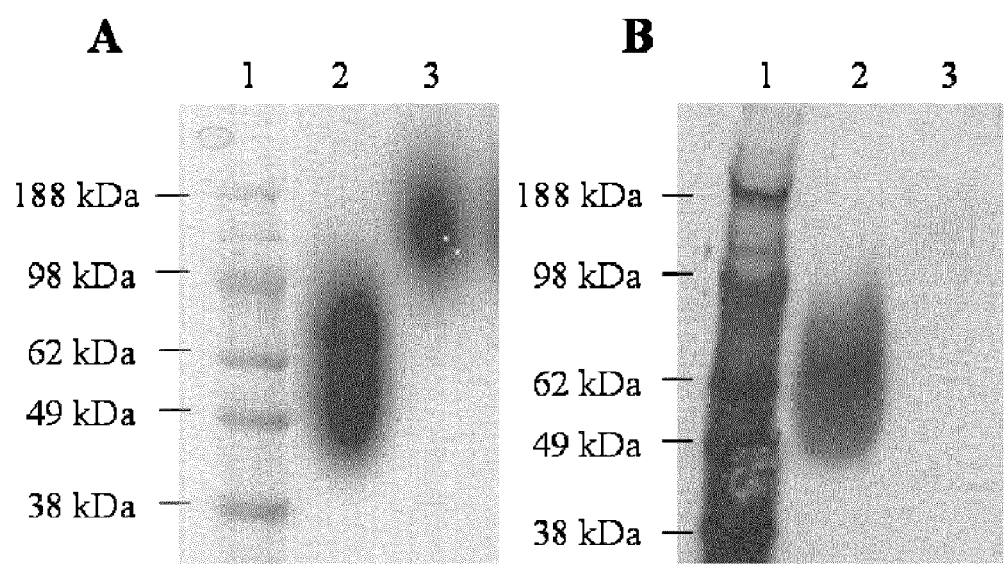

FIG. 2 shows the SDS-PAGE of enzymatically digested cell wall extracts. A Staining with periodic acid and Schiff's reagent (PAS). B Staining with Stains All. Lane 1: molecular mass marker; lane 2: *E. faecalis* V583 wild type; lane 3: *E. faecalis* V583Δ1172.

Figure 3:
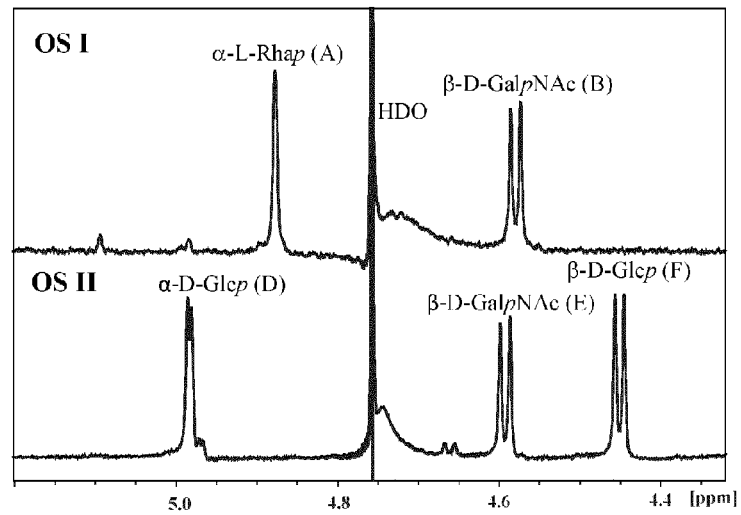
Figure 3:
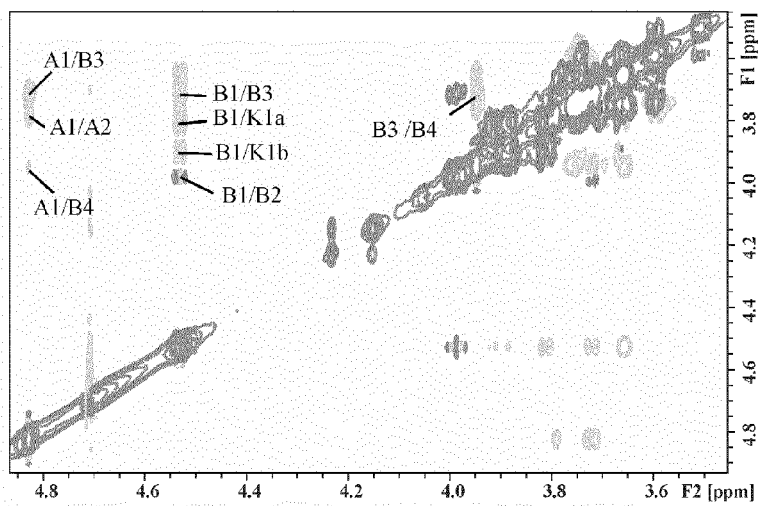
Figure 3:
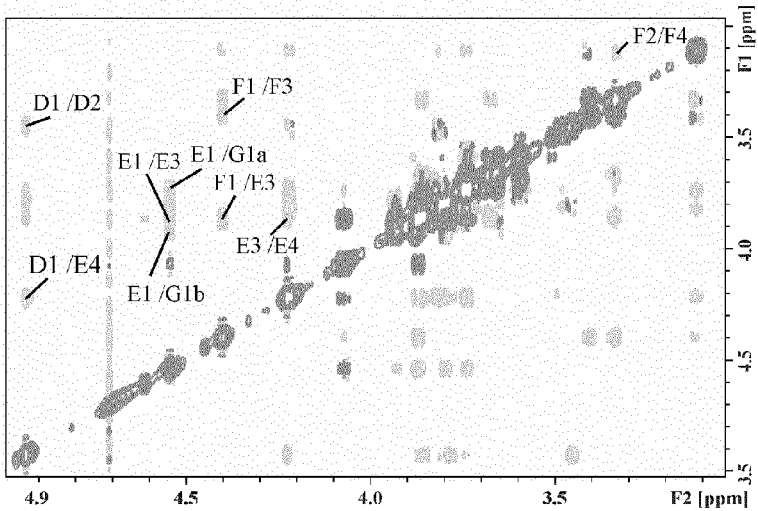

FIG. 3 shows the NMR spectroscopy of two preferred oligosaccharides (OS) I and II of the present invention. A $^1$H NMR spectra of the anomeric region of OS I and OS II. ROESY spectra of V583 wt OS I (B) and OS II (C) are shown below. Positive signals are depicted in green indicating $^1$H,$^1$H connectivities through covalent bonds, negative signals are depicted in blue indicating $^1$H,$^{1H}$ ones through the space. All measurements were conducted at 27° C. in $D_2O$ at 700 MHz with the internal standard acetone ($\delta_H$ 2.225).

FIG. 4 shows the structures of OS I (A) and OS II (B).

EXAMPLES

Methods and Materials

Bacterial Strains, Growth Conditions, and Medium

*E. faecalis* was cultivated at 37° C. without agitation in tryptic soy broth (TSB) (Carl Roth, Karlsruhe) which was supplemented with the respective antibiotics as indicated. Short term cultures were grown on tryptic soy agar (TSA) and stored at 4° C. Cultures for isolation of enterococcal cell wall polysaccharides were grown to stationary phase for 18 h and harvested by centrifugation. *E. coli* cultures were cultivated aerobically in Luria Bertani (LB) medium (Carl Roth, Karlsruhe) which was supplemented with antibiotics as indicated.

Construction of an EF1172 Gene Insertion Mutant in *E. faecalis* V583

A targeted insertion mutant of gene EF_1172 in *E. faecalis* V583 was done as described by Rigottier-Gois et al. (Rigottier-Gois L, Alberti A, Houel A, Taly J-F, Palcy P, Manson J, et al. Large-Scale Screening of a Targeted *Enterococcus faecalis* Mutant Library Identifies Envelope Fitness Factors. PLoS ONE. 2011 Dec. 15; 6(12):e29023), and the localization of the targeted insertion was verified by PCR and Southern blot as described previously.

Sera and Abs in Complement Binding Studies

Normal pooled human serum was obtained from healthy volunteers, who gave informed consent. Baby rabbit serum was obtained from Cederlane Laboratories. Clq-depleted serum was purchased from Quidel. Heat-inactivation of serum was performed by incubation for 20 min at 56° C. Serum was depleted of specific Ab to *E. faecalis* V583 by absorption with bacterial cells at 4° C. for 60 min. After absorption, bacteria were pelleted by centrifugation and the supernatant was passed through a 0.2 µm filter.

Opsonophagocytic Killing Assay

Bacterial opsonophagocytosis by human white blood cells (WBCs) was measured as described previously (Theilacker C, et al. Serodiversity of Opsonic Antibodies against *Enterococcus faecalis*-Glycans of the Cell Wall Revisited. PLoS ONE. 2011; 6(3):e17839). Briefly, bacterial strains were grown to mid-logarithmic phase ($OD_{600}$=0.4) in TSB and diluted with RPMI supplemented with 15% fetal calf serum. WBCs were purified from the blood of healthy volunteers by sedimentation with heparin-dextran buffer and remaining erythrocytes were removed by hypotonic lysis in 1% $NH_4Cl$ solution. Baby rabbit serum diluted 1:15 served as complement source. To remove natural Abs against target strains the complement was absorbed with *E. faecalis* V583 as described above. Rabbit serum raised against heat-killed *E. faecalis* V583 at a dilution of 1:2500 served as Ab source. In control tubes, Ab, complement, or PMNs were omitted from the assay. For the measurement of opsonophagocytosis, equal volumes of $2.5\times10^6$ PMNs, $2.5\times10^6$ CFUs bacteria, complement and heat-inactivated immune rabbit serum were combined. After 90 min incubation, the reaction was stopped at 4° C., PMNs were lyzed by hypotonic lysis, and viable cell counts were determined by plating of serial dilutions.

Phagocytosis Assay

The phagocytosis assay was performed as described with modifications (Rooijakkers S H, et al. Immune evasion by a staphylococcal complement inhibitor that acts on C3 convertases. Nat Immunol. 2005 September; 6(9):920-7). Human pooled serum was absorbed with the *E. faecalis* as described above and diluted in RPMI with addition of 0.05% human serum albumin (HSA) to the respective concentration. Next, $7.5\times10^4$ freshly isolated human neutrophils and $7.5\times10^5$ FITC-labeled, heat-killed *E. faecalis* V583 wild type or *E. faecalis* V583Δ1172 were added and incubated for 15 min at 37° C. while shaking at 750 rpm. The reaction was stopped by adding 1.5% ice-cold paraformaldehyde in RPMI 0.1% HSA. Phagocytosis was analyzed by flow cytometry (FACSCalibur; Becton Dickinson) measuring fluorescence of 10,000 gated neutrophils. Heat-inactivated serum was used as a control for complement-independent phagocytosis.

C3b Deposition on *E. faecalis*

*E. faecalis* strains were grown to an $OD_{600}$ of 0.5 in TSB and washed in HEPES++ buffer (20 mM HEPES, 140 mM NaCl, 5 mM $CaCl_2$, 2.5 mM $MgCl_2$) with 0.1% BSA. $12.5\times10^5$ bacteria were incubated with serum for 30 min while shaking at 900 rpm. Bacteria were washed with PBS supplemented with 0.1% BSA. C3b deposition was detected using mouse anti-human C3d Abs (Quidel) and FITC-conjugated goat anti-mouse IgG (Protos). Fluorescence of 10,000 bacteria was measured by flow cytometry. Classical and lectin pathway was abolished by incubation bacteria with complement in the presence HEPES++ buffer plus 5 mM $MgCl_2$ and 10 mM EGTA, pH 7.5. For specific inactivation of the classical pathway, Clq depleted serum was used (Quidel). The C3 convertase complex (C4bC2a) was measured using a monoclonal antibody to human C4/C4d (Quidel) and goat polyclonal anti-mouse FITC conjugate as secondary antibody (Dako). MASP-2 deposition was detected using a goat polyclonal anti-MASP-2 Ab (Santa Cruz Biotechnology).

Isolation of Cell-Wall Polysaccharide

For isolation of enterococcal cell wall polysaccharides, bacteria were cultivated as described above. Bacteria were washed and resuspended in digestion buffer (PBS plus 20 mM $CaCl_2$, 20 mM $MgCl_2$, $NaN_3$ 0.05%) and cleaved enzymatically with mutanolysin (0.01 mg/mL) and lysozyme (0.5 mg/mL) at 37° C. for 18 h. Afterwards, insoluble material was removed by centrifugation and the supernatant was treated with nucleases (DNase I and RNase, final concentration 0.1 mg/mL) for 18 h at 37° C. Proteins were degraded by digestion with proteinase K (0.1 mg/mL) for 8 h at 56° C. The supernatant was extensively dialyzed (10 ku MMCO) against $H_2O$ and lyophilized. For size exclusion chromatography (SEC), the sample was dissolved in 50 mM ammoniumcarbonate buffer (pH 8.8; $NaN_3$ 0.02%) and applied on a Sephacryl S 200 column (1.6×100 cm, GE Healthcare). Hexose and phosphorus content were measured as described previously (Theilacker C, et al. Opsonic antibodies to *Enterococcus faecalis* strain 12030 are directed against lipoteichoic acid. Infect Immun. 2006 October; 74(10):5703-12), and positive fractions eluting at a $K_{av}$ of 0.29 and 0.31, respectively, were combined, dialyzed and lyophilized. The resulting material was dissolved in 20 mM $NaHCO_3$ (pH 8.0, $NaN_3$ 0.02%) and subjected to anion-exchange chromatography (Q Sepharose FF, GE Healthcare).

To cleave phosphodiester bonds, 10 mg sample was dissolved in 50 µL 48% HF and incubated at 4° C. for 2 d. The material was neutralized and separated by SEC on Sephadex G50 (1.6×100 cm column, Biorad). Fractions of the lowest molecular mass were further purified by SEC on Biogel P2 (1×120 cm Column, Biorad), followed by high-performance anion-exchange chromatography (HPAEC, Dionex) applying a CarboPak PA 100 column (9×250 mm) and an ED50 electrochemical detector (Dionex). Data analysis was performed using the Chromeleon Version 6.6 software.

SDS-PAGE

For SDS-PAGE of crude enterococcal cell wall carbohydrates 40 mL culture was spun down and the pellet was digested with mutanolysin, lysozyme, nucleases and proteinase K as described above. After extensive dialysis against $H_2O$, 100 µg of the lyophilized material was separated by a precasted 10% Nupage Novex BisTris gel (Invitrogen) in Nupage SDS-MES running buffer (Invitrogen). Carbohydrates were stained with Stains All or periodic acid Schiff's (PAS) reagent as described previously (Theilacker C, Kaczynski Z, Kropec A, Sava I, Ye L, Bychowska A, et al. Serodiversity of Opsonic Antibodies against *Enterococcus faecalis*-Glycans of the Cell Wall Revisited. PLoS ONE. 2011; 6(3):e17839; Hancock L E, Gilmore M S. The capsular polysaccharide of *Enterococcus faecalis* and its relationship to other polysaccharides in the cell wall. Proc Natl Acad Sci USA. 2002 Feb. 5; 99(3):1574-9).

General and Analytical Chemical Methods

Qualitative and quantitative analyses of neutral sugars were performed by gas chromatography (GC) of the hydrolyzed and peracetylated alditol acetates as described previously (Haseley S R, Holst O, Brade H. Structural and serological characterisation of the O-antigenic polysaccharide of the lipopolysaccharide from *Acinetobacter haemo-*

*lyticus* strain ATCC 17906. Eur J Biochem. 1997 Mar. 15; 244(3):761-6). GC separations were conducted with an Agilent GC System (6890N) equipped with a poly-(5%-diphenyl-95%-dimethyl)-siloxan SPB-5-capillary column (30 m, 0.32 mm i.d.). Signals were detected by flame ionization and analyzed with the Agilent ChemStation Version B 01.01 software. The absolute configuration of sugars was determined by GC of peracetylated (S)-2-butanolglycosides.

Methylation analysis was carried out by analyzing the partially methylated alditol acetates of the HF-treated material by GC-MS (Ciucanu I, Kerek F. A Simple and Rapid Method for the Permethylation of Carbohydrates. Carbohydrate Research. 1984; 131(2):209-17). Briefly, 150 µg of the HF-treated lyophilized material was three times methylated (methyl iodide) in water-free DMSO (stored over molecular sieve [4 Å]) with addition of powdered NaOH. The mixture was kept for 1 h at 20° C. stirring. Then, the methylated polysaccharides were extracted three times with 2 mL chloroform, dried and hydrolyzed with 4 M $CF_3COOH$ for 4 h at 100° C. Subsequently the material was evaporated with deionized $H_2O$ to remove residual $CF_3COOH$ and reduced with sodium borodeuteride (18 h in the dark). Peracetylation was performed as described above, followed by GC-MS analysis.

Nuclear Magnetic Resonance Spectroscopy

Nuclear magnetic resonance (NMR) spectroscopy was conducted on an Avance III Bruker 700 MHz Ultrashield Plus spectrometer, applying standard software (Bruker). The working frequencies for $^1$H-NMR experiments were 700.75 MHz, for $^{13}$C-NMR experiments 176.20 MHz and for $^{31}$P-NMR experiments 283.67 MHz. For H-D exchange, samples were repeatedly solved in $D_2O$ (99.9%) and evaporated under nitrogen, and for final measurements the sample was solved in $D_2O$ (99.99%). All spectra were recorded at 27° C. Chemical shifts are assigned in ppm and calibrated according to values of acetone ($\delta_H$: 2.225; $\delta_C$: 31.45) used as internal standard.

Correlation spectroscopy (COSY), total correlation spectroscopy (TOCSY), nuclear-Overhauser-enhancement spectroscopy (NOESY) and rotating-frame nuclear-Overhauser-enhancement spectroscopy (ROESY) spectra were recorded with datasets (t2×t1) of 2048×512 bitpoints. TOCSY and NOESY experiments were conducted phase sensitive with mixing times of 400 ms and 180 ms respectively. Heteronuclear 2D $^1$H—$^{13}$C correlations were performed by heteronuclear multiple quantum coherence (HMQC), heteronuclear multiple bond correlation (HMBC), and heteronuclear single quantum correlation (HSQC) experiments with datasets of 4096×512 bitpoints.

Results

*E. faecalis* Mutants Impaired in WTA Biosynthesis are More Susceptible to Opsonophagocytosis in the Absence of Specific Ab Insertional mutants of genes with high homology to teichoic acid glycerol (tag) genes tagO (EF2198), tagA (EF1173) and tagB (EF1172) have been constructed previously (Table 1) (Rigottier-Gois L, Alberti A, Houel A, Taly J-F, Palcy P, Manson J, et al. Large-Scale Screening of a Targeted *Enterococcus faecalis* Mutant Library Identifies Envelope Fitness Factors. PLoS ONE. 2011 Dec. 15; 6(12): e29023).

TABLE 1

Analysis of homologies of *B. subtilis* W23 and *S. aureus* COL teichoic acid biosynthesis genes to *E. faecalis* V583 by the BLAST algorithm.

| | | *B. subtilis* | | *S. aureus* | | |
|---|---|---|---|---|---|---|
| | | % Id | % Si | % Id | % Si | Function |
| EF2198 | TagO | 24 | 40 | 41 | 65 | UDP-N-acetylglucosamine: undecaprenyl-P N-acetylglucosaminyl-1-P transferase |
| EF1173 | TarA | 38 | 60 | 33 | 59 | N-acetylglucosaminyl-diphospho-undecaprenol N-acetyl-mannosaminyl-transferase |
| EF1172 | TagB | 28 | 48 | 26 | 47 | glycerophosphotransferase |

The inventors studied these mutants in a heterologous opsonophagocytic killing assay using 1.7% baby rabbit serum depleted of specific Ab by absorption to the target strain as complement source (FIG. 1). *E. faecalis* V583 wild type was resistant to complement-dependent opsonophagocytosis by human neutrophils. Only after addition of specific Ab, bacteria were readily killed. In contrast, insertional mutants of *E. faecalis* in tagO (EF2198), tagA (EF_1173) and tagB (EF_1172) were highly susceptible to complement-mediated killing and the addition of specific Ab did not further promote opsonophagocytosis (FIG. 1, A). Next, the inventors incubated FITC-labeled, heat-killed *E. faecalis* cells with absorbed human serum to measure the uptake by human neutrophils by FACS analysis. At serum concentrations up to 10%, the rate of phagocytosed *E. faecalis* V583Δ1172 was much higher compared to wild type bacteria (FIG. 1B).

Inactivation of tagB (EF1172) in *E. faecalis* V583 Leads to Increased C3b Deposition by the Lectin Pathway To test whether higher phagocytic uptake of *E. faecalis* V583Δ1172 was due to increased complement deposition, the inventors measured the amount of C3b bound to bacterial cells by flow cytometry. Human serum depleted of specific Ab by absorption with the target strain was used as complement source. Compared to wild type bacteria, higher concentrations of C3b bound to *E. faecalis* V583Δ2198 (tagO homologue) and to *E. faecalis* V583Δ1172 (FIG. 1C) were detected. C3b is the final product of the classical, lectin and alternative pathway of complement activation. Classical and lectin pathway both lead to the formation of the C3 convertase complex C4bC2b, which cleaves C3 into C3a and C3b. $Ca^{2+}$ is an essential cofactor for the activation of classical and lectin pathway.

Sensitivity to Complement Induced Opsonophagocytic Killing is Associated with Altered Cell Envelope Carbohydrates To investigate this hypothesis, the inventors characterized the structure of the cell wall-associated polysaccharides of *E. faecalis* wild-type and V583Δ1172. To this end, cell wall fragments after depolymerization of peptidoglycan by mutanolysin and lysozyme were separated by SDS-PAGE and stained by PAS and Stains All (FIG. 2). SDS-PAGE of the cell wall fragments of the wild type strain revealed a broad band around 60 ku. In *E. faecalis* V583Δ1172, in contrast, this band migrated distinctly slower and was not stained by cationic dye Stains All, suggesting a loss of negative charge motifs (FIG. 2).

Cell Wall Extracts of *E. faecalis* V583Δ1172 Contain Less Phosphorus and Glucosamine but More Rhamnose Cell wall extracts of the *E. faecalis* V583 wild type and its insertional mutant V583Δ1172 were further purified by chromatography. First, the material was separated by SEC. Despite the different migration pattern on SDS PAGE, cell wall extracts of the wild type and mutant eluted at similar volumes in SEC, indicating a similar molecular mass. Material from E. faecalis V583Δ1172, however, contained less phosphorus. For further analysis, fractions of the major carbohydrate-containing peak were combined ($K_{Av}$ 0.30) and subjected to anion-exchange chromatography. Material from E. faecalis wild type eluted as a major, phosphorus-containing peak at 175 mM NaCl from Q Sepharose. In contrast, the major peak in E. faecalis V583Δ1172 did not bind to the anion-exchange column, again suggesting a loss of negative charge. Compositional analysis of the purified extracts revealed that polysaccharide of both strains contained Rha, Glc, GalN, GlcN, ribitol, and phosphate. Comparison of the molar ratios of sugars, ribitol and phosphate revealed that the V583Δ1172 polysaccharide contained approximately fourfold less galactosamine and ribitol, and app. 2.5-fold less phosphate compared to the wild type. On $^1$H NMR spectroscopy, anomeric proton signals of the cell wall polysaccharide of E. faecalis wild type and V583Δ1172 differed, but heterogeneity of the anomeric region precluded a detailed analysis without further degradation of the molecule.

Cell-Wall Polysaccharide of E. faecalis V583Δ1172 Lacks Covalently Bound WTA

To further investigate the structure of both cell-wall polysaccharides, phosphodiester bonds were hydrolyzed by aqueous HF and the hydrolysate was fractioned by SEC (Supplemental FIGS. 1 and 3 A). In comparison to the cell wall fragments of the wild type strain, the elution profile of the mutant polysaccharide lacked a low-molecular mass peak eluting near the total column volume. This low-molecular mass material from the wild type strain was further purified by size exclusion chromatography and compositional analysis was performed. It confirmed the presence of D-GalN, L-Rha, D-Glc, and ribitol as typical components of a ribitol-containing TA (Table 2). Further separation of this material by HPAEC revealed the presence of two different oligosaccharides designated OS I and OS II, which were then isolated by preparative HPAEC.

TABLE 2

Compositional analysis of accessory cell wall polymers of E. faecalis after dephosphorylation with HF and SEC on Sephadex G50. In E. faecalis V583Δ 1172 pool 3 was absent.

| | Rha | Glc | Ribitol | GlcN | GalN | Ala | Glu | Lys |
|---|---|---|---|---|---|---|---|---|
| V583 wt pool 1 | 2116 | 643 | N.D. | 280 | 154 | 112 | 28 | 28 |
| V583 wt pool 2 | 363 | 170 | 27 | 198 | 178 | 972 | 274 | 287 |
| V583 wt pool 3 | 589 | 690 | 1180 | N.D. | 1668 | 14 | 6 | 7 |
| V583Δ1172 pool 1 | 3337 | 762 | N.D. | 268 | 123 | 129 | 30 | 28 |
| V583Δ1172 pool 2 | 524 | 110 | N.D. | 10 | 6 | 64 | 16 | 16 |

N.D.: not detected.
Rha—rhamnose, Glc—glucose, GlcN—glucosamine, GalN—galactosamine, Ala—alanine, Glu—glutamine, Lys—lysine.
Concentrations are expressed as nmol/mg.

The $^1$H NMR spectrum of OS I (see FIG. 4) showed two different signals in the anomeric region, i.e., at δ 4.88 (A1) that was assigned as the anomeric proton of α-L-Rhap and at δ 4.58 (B1) which was annotated as anomeric proton of β-D-GalpN. The signal at δ 1.27 (A6) was assigned to the methyl protons of Rha. The $^1$H NMR spectrum of OS II (see FIG. 4) comprised three different signals in the anomeric region. One signal at δ 4.59 (E1) represented the anomeric proton of a β-D-GalpN residue, another at δ 4.98 was assigned to the anomeric proton of α-D-Glcp (D1), and that at δ 4.45 (F1) to the anomeric proton of β-D-Glcp. The $^1$H NMR spectra displayed signals at δ 2.06 (OS I) and δ 2.03 (OS II), indicating N-acetylation of GalpN in both samples. Thus, the corresponding structures were the trisaccharide α-L-Rhap-(1→3)-β-D-GalpNAc-(1→1)-ribitol for OS I and the branched tetrasaccharide α-D-Glcp-(1→4)-[β-D-Glcp-(1→3)-]β-D-GalpNAc-(1→1)-ribitol for OS II.

The invention claimed is:

1. A method for inducing an immune response to Enterococcus faecalis in a subject, the method comprising administering, to the subject an enterococcal cell wall component or an antibody that specifically recognizes the enterococcal cell wall component, wherein the enterococcal cell wall component is β-D-GalpNAc-ribitol having the following structure:

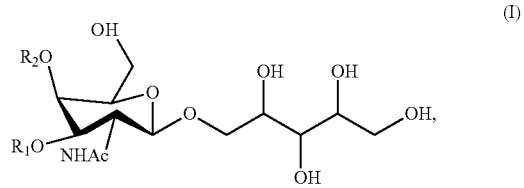

(I)

wherein $R_1$ is selected from β-D-Glcp and α-L-Rhap, and $R_2$ is selected from H and α-D-Glcp.

* * * * *